US00PP12417P2

(12) United States Plant Patent
Zaiger et al.

(10) Patent No.: US PP12,417 P2
(45) Date of Patent: Feb. 26, 2002

(54) CHERRY TREE NAMED 'REGAL LEE'

(76) Inventors: Chris Floyd Zaiger, 929 Grimes Ave.; Gary Neil Zaiger, 1907 Elm Ave.; Leith Marie Gardner, 1207 Grimes Ave.; Grant Gene Zaiger, 4005 California Ave., all of Modesto, CA (US) 95358

( * ) Notice: Subject to any disclaimer, the term of this patent is extended or adjusted under 35 U.S.C. 154(b) by 0 days.

(21) Appl. No.: 09/542,012

(22) Filed: Apr. 3, 2000

(51) Int. Cl.[7] ..... A01H 5/00
(52) U.S. Cl. ..... Plt./181
(58) Field of Search ..... Plt./181

*Primary Examiner*—Bruce R. Campell
*Assistant Examiner*—Anne Marie Grünberg

(57) ABSTRACT

A new and distinct variety of cherry tree (*Prunus avium*) with the following unique combination of desirable features that are outstanding in a new variety. The following features of the tree and its fruit are characterized with the tree budded on 'Mahaleb' Rootstock (non-patented), grown on Hanford sandy loam soil with Storie Index rating 95, in USDA Hardiness Zone 9, near Modesto, Calif., and with standard commercial cultural fruit growing practices, such as, pruning, thinning, spraying, irrigation and fertilization.

1. Heavy and regular production of fruit.
2. Fruit maturing in the early season.
3. Very firm fruit with good handling and storage ability.
4. The ability of the fruit to remain firm on the tree 14 days after maturity (shipping ripe).
5. Fruit with very good flavor and eating quality.
6. Fruit with attractive red skin color.
7. A low winter chilling requirement of approximately 500 hours at or below 45° F.

1 Drawing Sheet

BACKGROUND AND FIELD OF INVENTION

In the field of plant genetics we conduct an extensive and continuing plant breeding program which includes cherries. It is against this background of activities that the present low chilling cherry variety, 'Royal Lee', was originated. Asexual reproduction of the new and distinct variety of cherry tree was by budding to 'Mahaleb' Rootstock (non-patented), a standard rootstock for cherries in California, as performed by us in our experimental orchard located near Modesto, Calif., and shows that reproductions run true to the original tree and all characteristics of the tree and its fruit are established and transmitted through succeeding asexual propagations. The successful objective in the development of the variety was to reduce the winter chilling requirement, which provides a wider range of adaptability in which cherry trees will grow and produce commercial quality fruit.

SUMMARY OF THE VARIETY

The present new and distinct cherry tree is of large size, vigorous, upright growth, and has a low winter chilling requirement of approximately 500 hours below 45° F. The tree is further characterized by being a regular and productive bearer of medium to large size fruit with attractive red skin color, ripens in the early maturity season, and has very good flavor and eating quality. The fruit is further characterized by having very firm flesh with good handling and storage ability, and the ability to remain firm on the tree 14 days after maturity (shipping ripe). In comparison to 'Early Burlat' Cherry (non-patented), the new variety has a lower winter chilling requirement, blooming 11 days earlier and has the adaptability to produce fruit in more southern locations with less winter chilling hours, the fruit has firmer flesh and is approximately 6 days later in maturity.

ORIGIN OF THE VARIETY

The present new variety of cherry tree was developed by us in our experimental orchard located near Modesto, Calif., as an open pollinated seedling selection from the cherry selection 6HB488 (non-patented). Cherry selection 6HB488 originated as an open pollinated seedling selection of 17H143 (non-patented). The cherry selection 17H143 is a first generation cross between 26W232 (non-patented) and a lower chilling seedling of unknown parentage. The maternal parent 26W232 is a selected seedling from an open pollinated 'Bing' Cherry (non-patented). All numbered seedlings were selected by us to be used as future parents in our breeding program. A large group of these open pollinated seedlings were grown on their own root system, and maintained under careful observation by us, one early blooming seedling, with a low winter chilling requirement, which is the present variety, having especially desirable fruit characteristics, was selected for asexual reproduction and commercialization.

DESCRIPTION OF PHOTOGRAPH OF THE VARIETY

The accompanying color photographic illustration shows typical specimens of the foliage and fruit of the present new cherry variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of cherry tree, its flowers, foliage and fruit, as based on observations of specimens grown near Modesto, Calif., with color terminology (except those in common terms) in accordance with Reinhold Color Atlas by A. Kornerup and J. H. Wanscher.

Tree:

*Size.*—Large. Tree is maintained by pruning to 12 to 15 feet in height at maturity for economical harvesting of fruit.

*Vigor.*—Vigorous. Growing 5 to 6 feet in height the first growing season. During the first and second growing season, the upright growth is restricted by tying the branches selected for future scaffolds downward to create a wider crotch angle and spread the tree to the desired width of 12 to 14 feet at maturity. Growth rate will vary with type and depth of soil, cultural practices and climatic conditions.

*Productivity.*—Productive. Produces a heavy crop annually.

*Bearer.*—Regular. Has adequate fruit set annually for 10 years. Amount of fruit set varies with the number of pollinator trees per acre, climatic conditions and cultural practices.

*Form.*—Upright. After the first fruiting season the tree is usually pruned to control width and height.

*Density.*—Medium dense. The center branches are pruned during the dormant season to allow for greater air movement and sunlight to center of the tree to enhance fruit spurs, fruit color and brix.

*Hardiness.*—Tree grown in USDA Hardiness Zone 9. Winter chilling requirement is approximately 500 hours below 45° F.

Trunk:

*Size.*—Large. Circumference of 19½ inches measured at 24 inches above ground on a 8 year old tree.

*Texture.*—Medium rough. Varies with age of growth.

*Color.*—Brownish gray to brown (5-E-2) to (5-E-4).

Branches:

*Size.*—Medium. Average circumference of 8 inches measured at 40 inches above ground.

*Texture.*—Smooth to medium rough, varies with age of growth.

*Lenticels.*—Large. Medium number, an average of 17 lenticels in a 4 square inch area.

*Color.*—Grayish brown to brown (5-E-3) to (5-E-5).

Leaves:

*Size.*—Large. Average length 7½ inches. Average width 2⅛ inches.

*Form.*—Varies between ovate and lanceolate, pointed.

*Margin.*—Serrate.

*Thickness.*—Medium.

*Surface.*—Smooth.

*Petiole.*—Average length 2¼ inches. Medium thickness. Color — upper surface exposed to sun, brownish red (8-C-8), lower surface shaded, grayish green (29-D-6), varies with age and amount of direct sunlight.

*Glands.*—Reniform. Size — large. Number varies from 2 to 4. Average number 2. Located on upper portion of the petiole and lower portion of the leaf blade, primarily on upper portion of petiole. Color varies from ruby red to grayish ruby (12-D-8) to (12-E-7) on new immature leaves and darker red (10-D-8) on mature leaves.

*Color.*—Upper surface — green to dark green (28-F-6) to (28-F-8). Lower surface — dull green to grayish green (28-E-5) to (28-E-7).

Flower buds:

*Size.*—Large. Average length 23/32 inch. Averge diameter 19/64 inch.

*Form.*—Plump, conical, becoming elongated before opening.

*Color.*—Varies from white (10-A-1) to very light pinkish white (10-A-2) on upper surface of petals.

*Number per spur.*—Varies from 4 to 9, average 5.

*Peduncle.*—Average length 37/64 inch. Average width 1/16 inch.

*Hardiness.*—Hardy in all stone fruit growing areas of California.

Flowers:

*Blooming period.*—Mar. 1 to Mar. 10, 1997. Varies slightly with climatic conditions.

*Size.*—Large, showy. Average height 53/64 inch. Average width 1 15/16 inches.

*Petals.*—Shape — orbicular, alternately arranged with sepals. Surface — relatively smooth, edges smooth, slight cleft in center of apex. Size — average length 41/64 inch. Average width 43/64 inch. Color — varies from white to very light pinkish white on upper surface (10-A-1) to (10-A-2), fades with age.

*Pistil.*—Normally 1, varies from 1 to 2. Average length 11/64 inch. Surface — glabrous. Stigma approximately ⅛ inch below anthers. Color varies from greenish white to pale green (30-A-2) to (30-A-3).

*Stamens.*—Number averages 42. Average filament length 27/64 inch. Filament color white (30-A-1). Color of anthers — light yellow to yellow (3-A-5) to (3-A-7).

*Sepals.*—Number — 5. Arrangement — alternate with petals. Surface — inner surface glabrous. Outer surface glabrous. Size — average length 19/64 inch. Average width 11/64 inch. Color — upper surface varies from light green to grayish green (29-A-4) to (29-B-4). Lower surface varies from grayish green in center (29-B-4) to grayish red on outer surface (8-C-5).

*Pollen.*—Self sterile, pollenizer required. Abundant — full pollen sacs. Color varies from light yellow to yellow (3-A-5) to (3-A-7).

*Peduncle.*—Size — average length ⅝ inch. Average width 5/64 inch. Color varies from light green to grayish green (29-A-6) to (29-B-6).

*Fragrance.*—Very slight aroma.

Fruit:

*Maturity when described.*—Firm ripe (shipping ripe).

*Date of first picking.*—May 5, 1997.

*Date of last picking.*—May 12, 1997. Varies slightly with climatic conditions.

*Size.*—Medium to large. Comparatively uniform. Average diameter axially 15/16 inch. Average transversely in suture 1 inch. Average weight 9.3 grams. Weight and size varies slightly with soil fertility, crop load and climatic conditions.

*Form.*—Relatively uniform, globose to slightly oblate.

*Suture.*—Shallow, extends from base to apex. Relatively smooth.

*Ventral surface.*—Nearly rounded.

*Apex.*—Rounded to slight depression.

*Base.*—Retuse.

*Cavity.*—Rounded. Average depth 3/32 inch. Average breadth 3/16 inch.

Skin:

*Thickness.*—Medium.

*Texture.*—Medium, tenacious to flesh.

*Down.*—Wanting.

*Tendency to crack.*—None during dry weather. Slight tendency to crack during wet weather, varies with stage of fruit maturity.

*Color.*—Red to garnet red (11-E-6) to (11-E-8).

Stem of the fruit:

*Size.*—Average length 1 inch. Average width 3/32 inch.

*Color.*—Olive green to moss green (1-E-5) to (1-E-7).

Flesh:

*Ripens.*—Evenly.

*Texture.*—Very firm.

*Fibers.*—Small and tender.

*Aroma.*—Slight.

*Eating quality.*—Very good.

*Flavor.*—Very good.

*Juice.*—Moderate amount, enhances flavor, good balance between sugar and acid.

*Brix.*—17.7° average.

*Color.*—Pale red to red (11-A-3) to (11-C-7). Pit cavity — red to wine red (11-D-7) to (11-D-8).

Stone:

*Type.*—Clingstone.

*Size.*—Average length 7/16 inch. Average width 11/32 inch. Average thickness 1/4 inch.

*Form.*—Ovoid.

*Base.*—Slightly rounded.

*Apex.*—Round to slight apical point.

*Surface.*—Smooth. Small narrow ridges running along each side of the suture line and extends slightly beyond base on some stones.

*Sides.*—Varies from equal to unequal.

*Tendency to split.*—None.

*Color.*—Light tan to tan (5-B-2) to (5-B-5).

Use: Dessert. Market, local and long distance.

Keeping quality: Good. Fruit showed no internal browning or wooliness of flesh when stored for 21 days at 38° to 42° F.

Shipping quality: Good. Fruit showed minimal bruising or scarring of skin or flesh during packing and shipping.

Plant disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance/susceptibility has been observed. Any variety or selection observed during indexing of plant characteristics with abnormal fungus, bacterial, virus or insect susceptibility is destroyed and eliminated from our breeding program.

The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct variety of cherry tree, substantially as illustrated and described, characterized by its large size, vigorous, upright growth, a low winter chilling requirement of approximately 500 hours at or below 45° F., and being a regular and productive bearer of medium to large size, attractive red skin fruit that matures in the early season; the fruit is further characterized by its very firm flesh and has the ability to remain firm on the tree 14 days past maturity, very good flavor and eating quality and, in comparison to 'Early Burlat' Cherry (non-patented), the new variety of cherry tree blooms approximately 11 days earlier and the fruit has firmer flesh and is approximately 6 days later in maturity.

* * * * *

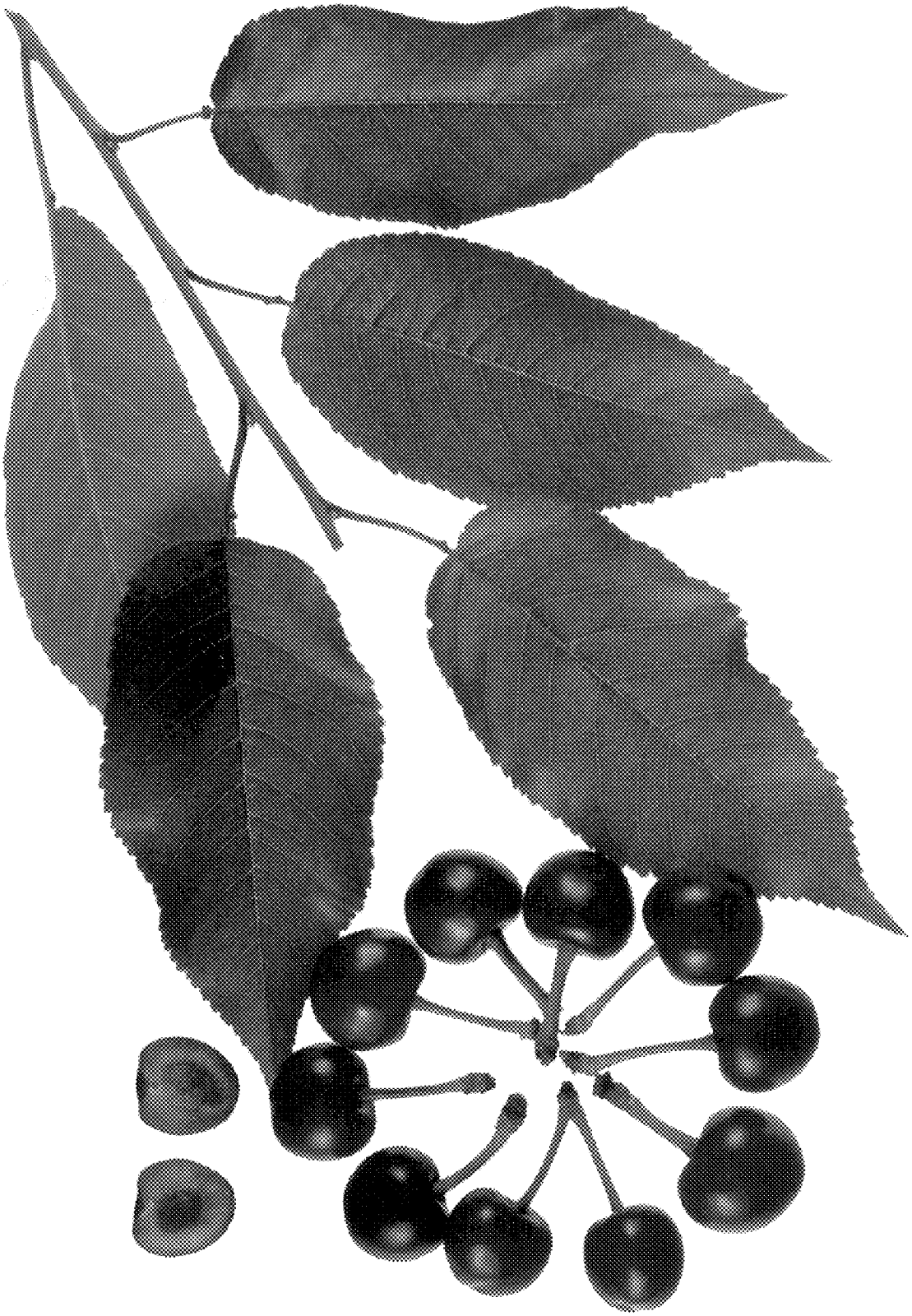

UNITED STATES PATENT AND TRADEMARK OFFICE

CERTIFICATE OF CORRECTION

PATENT NO. : PP 12,417 P2
DATED : February 26, 2002
INVENTOR(S) : Chris Floyd Zaiger et al.

It is certified that error appears in the above-identified patent and that said Letters Patent is hereby corrected as shown below:

Title page,
Item [54], Title, delete "CHERRY TREE NAMED 'REGAL LEE'" insert
-- CHERRY TREE NAMED ROYAL LEE --

Signed and Sealed this

Twenty-seventh Day of July, 2004

JON W. DUDAS
*Acting Director of the United States Patent and Trademark Office*